(12) United States Patent
Winkler et al.

(10) Patent No.: US 6,252,098 B1
(45) Date of Patent: Jun. 26, 2001

(54) ENHANCED SYNTHESIS OF RACEMIC METALLOCENES

(75) Inventors: Uwe F. Winkler; Meng-Sheng Ao, both of Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/586,818

(22) Filed: Jun. 5, 2000

(51) Int. Cl.⁷ .............................. C07F 17/00; C07F 7/00; B01J 31/00

(52) U.S. Cl. ............................... 556/11; 556/43; 556/53; 556/58; 534/11; 534/15; 502/103; 502/117; 526/160; 526/943

(58) Field of Search .................. 556/11, 43, 53, 556/58; 534/11, 15; 502/103, 117; 526/160, 943

(56) References Cited

U.S. PATENT DOCUMENTS

| | | | |
|---|---|---|---|
| 5,017,714 | 5/1991 | Welborn, Jr. | 556/12 |
| 5,036,034 | 7/1991 | Ewen | 502/117 |
| 5,145,819 | 9/1992 | Winter et al. | 502/117 |
| 5,296,434 | 3/1994 | Karl et al. | 502/117 |
| 5,302,733 | 4/1994 | Diefenbach et al. | 556/11 |
| 5,324,800 | 6/1994 | Welborn, Jr. et al. | 526/160 |
| 5,329,033 | 7/1994 | Spaleck et al. | 556/53 |
| 5,847,175 | 12/1998 | Strickler et al. | 556/11 |
| 5,883,278 | 3/1999 | Strickler et al. | 556/53 |

FOREIGN PATENT DOCUMENTS

WO 9912943 * 3/1999 (WO) .

* cited by examiner

*Primary Examiner*—Porfirio Nazario-Gonzalez
(74) *Attorney, Agent, or Firm*—Philip M. Pippenger

(57) ABSTRACT

Chiral metallocenes are prepared by reacting a salt of an asymmetric bis(cyclopentadienyl)-moiety-containing ligand with a tertiary heteroaromiatic amine adduct of a transition, lanthanide, or actinide metal halide in an organic solvent or diluent so as to produce said chiral metallocene.

15 Claims, No Drawings

ENHANCED SYNTHESIS OF RACEMIC METALLOCENES

The invention relates generally to the preparation of metallocenes which are useful as stereoregular olefin polymerization catalysts and more specifically to a process for metallizing cyclopentadienyl ligand salts with certain transition, lanthanide or actinide metal compounds which are tertiary heteroaromatic amine adducts of the metal halides.

As known in the art, metallocenes can be prepared by reacting a metal compound of the formula $MX_n$, where M is the metal, n is an integer of 1 to 6, depending upon the valence of M, and X is independently an anionic ligand group or a neutral Lewis base ligand group having up to 30 non-hydrogen atoms such as hydride, halo, alkyl, aryl, silyl, germyl, aryloxy, alkoxy, amide, and siloxy, with an alkali metal or a magnesium halide salt of a cyclopentadienyl ligand in a solvent such as an ether.

Chiral metallocenes are useful for the synthesis of polyolefins. Specifically, the racemic form of the metallocene provides stereoregular poly(alpha-olefins) in addition to being considerably more active than the meso form, which produces only atactic polymers. An efficient synthesis of chiral metallocenes that favors the formation of the racemic isomer at the metallation stage is desired. We have now found that by using certain tertiary heteroaromatic amine adducts of a metal halide in the reaction with the salt of the cyclopentadienyl ligand, enhanced formation of the racemic isomer and/or better product yields can be produced, especially by using a hydrocarbon reaction solvent or diluent and conducting the reaction at ambient room temperatures.

In accordance with this invention there is provided a process for preparing a chiral metallocene, said process comprising reacting a salt of an asymmetric bis(cyclopentadienyl) moiety-containing ligand with a tertiary heteroaromatic amine adduct of a transition, lanthanide or actinide metal halide in an organic solvent or diluent so as to produce said chiral metallocene.

Chiral metallocenes which can be prepared in accordance with the process of the invention preferably contain a metal from Groups 3–10, or the lanthanide and actinide series of the Periodic Table of the elements and, more preferably a Group 4 to 6 transition metal, which is coordinated with a ligand containing a pair of cyclopentadienyl moieties, at least one of which is asymmetric, which moieties are stereorigid such as by being joined by a bridging group. In this connection, the metals are identified herein with reference to the IUPAC Periodic Table of the Elements as set forth in the Feb. 4, 1985 issue of Chemical & Engineering News. The cyclopentadienyl moieties can be substituted with one or more groups, such as halogen, amino, mercapto, phosphino, and $C_1$ to $C_{20}$ hydrocarbyl, silahydrocarbyl, or halohydrocarbyl and the like and can include moieties which are condensed, multi-ring structures such as, for example, indenyl, benzoindenyl, or fluorenyl, which structures can be hydrogenated and/or further substituted. The other groups on the metal atom usually include hydride, halogen, hydrocarbyl or halohydrocarbyl having up to about 6 carbons. Such chiral metallocenes, and their use as catalysts in forming isotactic olefin polymers are described, for example, in U.S. Pat. Nos. 5,017,714; 5,036,034; 5,145,819; 5,296,434; 5,324,800 and 5,329,033, whose disclosures are incorporated herein by reference. Typical bridging groups include silicon containing bridges of 1–4 atoms selected from silanylene, silaalkylene, oxasilanylene and oxasilaalkylene, such as, dimethylsilanylene. The chiral metallocenes are mixtures of racemic diasteriomers which have no plane of symmetry. In contrast, the meso isomers have a plane of symmetry running through the metal between the rings and are, therefore achiral.

Specific, non-limiting examples of chiral metallocenes include racemic:
[1,1'-dimethylsilanylenebis(3-methylcyclopentadienyl)]zirconium dichloride;
[1,1'-dimethylsilanylenebisindenyl]zirconium dichloride;
[1,1'-dimethylsilanylenebis(4,5,6,7-tetrahydroindenyl)]zirconium dichloride;
[1,1'-(1,1,2,2-tetramethyldisilanylene)bis(3-methylcyclopentadienyl)]zirconium dichloride;
[1,1'-(1,1,2,2-tetramethyldisilanylene)bis(4,5,6,7-tetrahydroindenyl)]zirconium dichloride;
[1,1'-dimethylsilanylenebis(3-trimethylsilanylcyclopentadienyl)]zirconium dichloride;
[1,1'-(1,1,2,2-tetramethyldisilanylene)bis(3-trimethylsilanylcyclopentadienyl]zirconium dichloride;
[1,1'-(1,1,3,3-tetramethyldisilanylene)bis(4,5,6,7-tetrahydroindenyl)]zirconium dichloride;
[1,1'-(1,1,4,4-tetramethyl-1,4-disilanylbutylene)bis(4,5,6,7-tetrahydroindenyl)]zirconium dichloride;
[1,1'-(2,2-dimethyl-2-silapropylene)bis(3-methylcyclopentadienyl)]zirconium dichloride;
[1,1'-dimethylsilanylenebis(3-metbylcyclopentadienyl)]titanium dichloride;
[1,1'-dimethylsilanylenebisindenyl]titanium dichloride;
[1,1'-dimethylsilanylenebis(4,5,6,7-tetrahydroindenyl)]titanium dichloride;
[1,1'-(1,1,2,2-tetramethyldisilanylene)bis(3-methylcyclopentadienyl)]titanium dichloride;
[1,1'-(1,1,2,2-tetramethyldisilanylene)bis(4,5,6,7-tetrahydroindenyl)]titanium dichloride;
[1,1'-dimethylsilanylenebis(3-trimethylsilanylcyclopentadienyl)]titanium dichloride;
[1,1'-(1,1,2,2-tetramethyldisilanylene)bis(3-trimethylsilanylcyclopentadienyl)]titanium dichloride;
[1,1'-(1,1,3,3-tetramethyldisilanylene)bis(4,5,6,7-tetrahydroindenyl)]titanium dichloride;
[1,1'-(1,1,4,4-tetramethyl-1,4-disilanylbutylene)bis(4,5,6,7-tetrahydroindenyl)]titanium dichloride;
[1,1'-(2,2-dimethyl-2-silapropylene)bis(3-methylcyclopentadienyl)]titanium dichloride;
[1,1'-dimethylsilanylenebis(3-methylcyclopentadienyl)]hafnium dichloride;
[1,1'-dimethylsilanylenebisindenyl]hafnium dichloride;
[1,1'-dimethylsilanylenebis(4,5,6,7-tetrahydroindenyl)]hafnium dichloride;
[1,1'-(1,1,2,2-tetramethyldisilanylene)bis(3-methylcyclopentadienyl)]hafnium dichloride;
[1,1'-(1,1,2,2-tetramethyldisilanylene)bis(4,5,6,7-tetrahydroindenyl)]hafnium dichloride;
[1,1'-dimethylsilanylenebis(3-trimethylsilanylcyclopentadienyl)]hafnium dichloride;
[1,1'-(1,1,2,2-tetramethyidisilanylene)bis(3-trmethylsilanylcyclopentadienyl)]hafnium dichloride;
[1,1'-(1,1,3,3-tetramethyldisilanylene)bis(4,5,6,7-tetrahydroindenyl)]hafnium dichloride;
[1,1'-(1,1,4,4-tetramethyl-1,4-disilanylbutylene)bis(4,5,6,7-tetrahydroindenyl)]hafnium dichloride;
[1,1'-(2,2-dimethyl-2-silapropylene)bis(3-methylcyclopentadienyl)]hafnium dichloride;
dimethylsilylbis(1-(2-methyl-4-ethylindenyl))zirconium dichloride;
dimethylsilylbis(1-(2-methyl-4-isopropylindenyl))zirconium dichloride;

dimethylsilylbis(1-(2-methyl-4-tert-butylindenyl)) zirconium dichloride;
methylphenylsilylbis(1-(2-methyl-4-isopropylindenyl)) zirconium dichloride;
dimethylsilylbis(1-(2-ethyl-4-methylindenyl))zirconium dichloride;
dimethylsilylbis(1-(2,4-dimethylindenyl))zirconium dichloride;
dimethylsilylbis(1-(2-methyl-4-ethylindenyl))zirconium dimethyl;
dimethylsilyl(2-methyl-4,5,6,7-tetrahydro-1-indenyl)$_2$zirconium dichloride;
dimethylsilylbis(2-methyl-4,5-benzoindenyl)zirconium dichloride;
ethylene(2-methyl-4,5,6,7-tetrahydro-1-indenyl)$_2$zirconium dichloride;
dimethylsilyl(2-methyl-4,5,6,7-tetrrhydro-1-indenyl)$_2$dimethyl zirconium;
phenyl(methyl)silyl(indenyl)$_2$zirconium dichloride;
dimethylsilyl(2,3,5-trimethyl-1-cyclopentadienyl)$_2$zirconium dichloride;
dimethylgermyl(indenyl)$_2$zirconium dichloride;
ethylene(indenyl)$_2$zirconium dichloride;
methylene(3-t-butyl-1-cyclopentadienyl)$_2$zirconium dichloride;
dimethylsilyl(4,7-dimethyl-1-indenyl)$_2$zirconium dichloride;
dimethylsilanylbisindenylthorium dichloride; and
dimethylsilanylbisindenyluranium dichloride.

The metallocenes are prepared by first deprotonating the appropriate ligand compound using an alkali metal, an alkali metal salt, a magnesium salt or a Grignard reagent to form an alkali metal, magnesium or magnesium halide salt of the ligand. Examples of deprotonizing agents include Na powder, RLi, NaH, LiH and RMgX, where R is $C_1$ to $C_{10}$ hydrocarbyl and X is halogen. Preferred are alkyllithium compounds such as methyllithium, n-butyllithium, s-butyllithium, t-butyllithium, phenyllithium and the like.

Suitable reaction solvents for the deprotonation reaction are aliphatic or aromatic hydrocarbon or halocarbon solvents and acyclic or cyclic ethers. Mixed ether and hydrocarbon or halohydrocarbon solvents in ratios of from about 9:1 to 1:9 by volume ether to hydrocarbon solvent and, preferably, 4:1 to 1:2 provide satisfactory results. Examples of suitable solvents include diethyl ether, tetrahydrofuran (THF), ethylene glycol dimethyl ether, hexanes, cyclohexane, heptane, pentane, toluene, benzene, xylene, chlorobenzene and the like.

The ligand salt, such as the dilithium salt, from the deprotonation is reacted with a tertiary heteroaromatic amine adduct of a transition, lanthanide or actinide metal compound, preferably a tertiary heteroaromatic amine adduct of a metal halide, in order to form the racemic metallocene. Suitable heteroaromatic amines for forming the adducts which are effective to provide metallocenes with an enhanced yield of racemic isomer, include such compounds as pyridine, α-picoline, β-picoline, γ-picoline, quinoline, isoquinoline, quinaldine, acridine, and the like. The preferred heteroaromatic amine is pyridine. A metal chloride to heteroaromatic amine ratio of 1:0.5 to 1:5 provides improved yields of the racemic metallocene. About equimolar to about a 10% excess of heteroaromatic amine is preferably used. Preferably, the heteroaromatic amine adduct of the metal is formed prior to mixing it with the ligand.

Non-limiting examples of transition, lanthanide and actinide metals include Ti, Zr, Hf; V, Cr, La, Ce, Th, U and the like. Preferred for catalyst use are the Group 4 metals Ti, Zr and Hf.

The adducts can be prepared in hydrocarbon solvents such as those named above for the deprotonation reaction and, preferably toluene. The adduct may be separated from the solvent, such as by filtration, or the adduct in the solvent can be used in forming the bridged metallocene, i.e., in the metallation reaction. In the case of zirconium metallocenes, mixtures of TBF and toluene have provided good yields of racemic isomer enriched product.

In carrying out the metallation reaction, a mixed hydrocarbon/ether solvent (toluene/THF) reaction medium is preferably used. The metallation reaction temperature is not critical and can range from about −20 to 120° C. and, preferably, from about 0 to 60° C. Stoichiometric to about a 10% excess amount of metal adduct to ligand salt is preferably used. A small amount of metallocene product (e.g., amounts which are about 0.05 to about 5 wt. % of the metal adduct) and/or ether solvent (THF) (preferably amounts which are about 1 to about 20 wt. % based on total solvent) may be added to the adduct slurry prior to the metallation reaction.

If desired, the reaction can be carried out by mixing together (i) a solution of a salt of an asymmetric bis(cyclopentadienyl)-moiety-containing ligand (in whatever chemical form it exists while in such solution), to (ii) an organic liquid medium containing a solution or slurry of a tertiary heteroaromatic amine adduct of a transition, lanthanide or actinide metal halide (in whatever chemical form it exists while in such solution or slurry), where at least 50 weight percent of the liquid solvent of the solution of (i) is one or more liquid aliphatic or cycloaliphatic polyethers, and at least 50 weight percent of the liquid solvent or diluent of the solution or slurry of (ii) is one or more liquid aliphatic, cycloaliphatic or aromatic hydrocarbons. Typically, the balance, if any, of the liquid solvent of the solution of (i) is composed of one or more liquid hydrocarbons, which can be aliphatic, cycloaliphatic and/or aromatic hydrocarbons. Examples of such polyethers include 1-ethoxy-2-methoxyethane, 1,2-diethoxyethane, 1-tert-butoxy-2-ethoxyethane, 1-tert-butoxy-2-methoxyethane, dimethyl ether of diethylene glycol, diethyl ether of diethylene glycol, tert-butyl methyl ether of diethylene glycol, dimethyl ether of triethylene glycol, 1,3-dioxolane, 2-methyl-1,3-dioxolane, 1,3-dioxane, and like liquid hydrocarbyl polyethers. As between the aliphatic and cycloaliphatic polyethers, the aliphatic polyethers are more preferred and of the latter, 1,2-dimethoxyethane (glyme) is especially preferred. The salt of the asymmetric bis(cyclopentadienyl)-moiety-containing ligand can be preformed and added to or otherwise blended with the one or more polyethers being used, or the asymmetric bis(cyclopentadienyl)-moiety-containing ligand can be formed in situ in such polyether or polyethers being used. Likewise before, during and/or after forming some of the asymmetric bis(cyclopentadienyl)-moiety-containing ligand in situ in the polyether or polyethers being used, additional preformed asymmetric bis(cyclopentadienyl)-moiety-containing ligand can be added to or otherwise blended with the polyether or the partially formed ligand solution.

By the same token, the balance, if any, of the liquid solvent or diluent of the solution or slurry of (ii) in the immediately preceding paragraph can be composed of one or more liquid aliphatic and/or cycloaliphatic hydrocarbons, or one or more liquid ethers and/or polyethers, or mixtures of one or more such hydrocarbons and one or more such ethers, and even more preferably the solvent or diluent used in the formation of the solution or slurry of (ii) is essentially entirely one or more such liquid hydrocarbons. Examples of such hydrocarbons include one of more of the liquid hexanes, heptanes, octanes, nonanes, decanes, undecanes, dodecanes, cyclohexane, methylcyclohexane, one or more liquid dimethylcyclohexanes, benzene, toluene, one or more of the xylenes, ethylbenzene, propylbenzene, one or more of the diethylbenzenes, butylbenzene, pentylbenzene, tetrahydronaphthalene, and similar liquid paraffinic, cycloparaffinic or aromatic hydrocarbons, and mixtures of any such substances including gasoline fractions, BTX, petroleum ethers, and the like. The aromatic hydrocarbons are preferred for this use, and of these the mononuclear aromatic hydrocarbons having from 6 to about 8 carbon atoms are more preferred. Toluene is particularly preferred. The tertiary heteroaromatic amine adduct of the transition, lanthanide or actinide metal halide can be preformed and added to or otherwise blended with the one or more hydrocarbons being used, or the adduct can be formed in situ in such hydrocarbon or hydrocarbons being used. Likewise before, during and/or after forming some of the adduct in situ in the hydrocarbon(s) being used, additional preformed adduct can be added to or otherwise blended with the hydrocarbon(s) or the partially formed adduct solution or slurry.

Preferably, the solution of (i)—i.e., the above ligand solution—is added to the solution or slurry of (ii)—ie., the above adduct solution or slurry. This embodiment of the invention is applicable to synthesis of chiral bridged metallocenes of transition, lanthanide and actinide metal halides in general, and preferably is used in connection with reactions with halides (preferably chlorides or bromides) of Group 4–6 metals, and especially in connection with formation of chiral bridged zirconium and hafnium metallocenes.

The invention is further illustrated by, but is not intended to be limited to, the following examples.

EXAMPLE 1

A. Preparation of lithium indenide (Li-Ind)

Under $N_2$ a mixture of 51.6 g (0.115 mole) of technical grade indene (92.5% by GC analysis, pre-purified by a neutral alumina column), 186.3 g of dry diethyl ether and 8.0 g of dried (over 4 Å molecular sieve) toluene was placed in a 1-L flask. The flask was equipped with an agitator, a condenser and thermometer. To the mixture a total of 172 mL (0.4316 mole) of n-butyllithium (2.5 M in hexanes) was added dropwise in 2 portions. The pot temperature was allowed to raise to reflux (38° C.) during the addition. When 150 mL of butyllithium were added, the addition was stopped and the analysis (NMR) of the mixture indicated that 22 mL more of butyllithium were needed to finish the reaction. After feeding the calculated amount of butyllithium, the final analysis of the reaction mixture showed 99% conversion and 99% yield of lithium-indenide (Li-Ind). The mixture was used as such for the next reaction.

B. Preparation of dimethylsilylbis(indene)

The Li-Ind reaction mixture from above was cooled in an ice bath. At pot temperature 5° C., a total of 26.3 g (0.2037 mole, based on the contained Li-Ind determined) of dichlorodimethylsilane was added dropwise. At the time when 20 g of the silane were added, the addition was stopped and the mixture was allowed to warm up to room temperature. The reaction was analyzed (NMR in deuterobenzene) and calculated that 4 g more of the silane were needed to finish the reaction. After adding the calculated amount of silane, the reaction was analyzed to have 98% conversion (NMR) and 90% yield (GC). The mixture was filtered through a dried Celite 545 bed (in a drybox) to remove solid LiCl and the solids were washed with ether (65 g). The combined filtrate and washes were further treated with butyllithium as described below.

C. Preparation of the dilithium salt of dimethylsilylbis(indene)etherate

To the combined filtrate and washes of the above reaction was added 180 mL (0.450 mole, 5% excess) of n-butyllithium (2.5 M in hexanes) dropwise. The pot temperature was allowed to raise to reflux (38° C.). The solid dilithium salt of dimethylsilylbis(indene)etherate started to precipitate out at about 50% addition. At the end of the addition, a sample of the supenatant liquid was analyzed by NMR to make sure all the starting material and intermediate were reacted. When no more dimethylsilylbis(indene) or monolithium salt of dimethylsilylbis(indene) was left, the pot was cooled down to room temperature and then diluted with 137 g of hexanes. The precipitated solids were filtered (in a dry box), washed with ether and dried to give 61 g of the dilithium salt of dimethylsilylbis(indene)etherate in 80% yield as off-white fine solids. The lithium complex was confirmed by NMR (in THF-d8 solvent) and analyzed by acid-base titration for weight percent (97%).

D. Preparation of dimethylsilyl-bis(indenyl) zirconium dichloride

In a drybox a 250 mL flask, equipped with a stir bar, is charged with $ZrCl_4$ (2.58 g, 11.07 mmol) and 10 g toluene. To this slurry is added 1.8 g anhydrous pyridine (22.7 mmol). The colorless suspension is stirred for 2 hours. Then a solution of the dilithium salt of dimethylsilylbis(indene) etherate (4.145 g, 11.07 mmol) in 13.7 g anhydrous THF is added dropwise. The color of the slurry changes immediately to yellow, later orange. After ca. 25% of the solution has been added, the consistency of the solids change from amorphous to being more crystalline. After complete addition, which takes about 1 hour, the mixture is stirred an additional 16 hours, Then the reaction mixture is filtered through a medium glass frit. The yellow solid is washed with 5 g of anhydrous THF, then dried in vacuum. The green filtrates are discarded. Yield: 4.15 g dimethylsilylbis (indenyl)zirconium dichloride (83.6%).

EXAMPLE 2

Preparation of dimethylsilylbis(indenyl)zirconium dichloride 1-liter 4 neck flask is charged in the drybox with $ZrCl_4$ (37.35 g, 160.27 mmol) and 139 g toluene. Then the flask is taken outside and an overhead stirrer is put in place, as well as a thermometer to monitor the temperature inside the flask. The suspension is stirred for 10 minutes, then 27 g anhydrous pyridime (341 mmol) are added. The mixture is stirred for 2 more hours. Then a solution of the dilithium salt of dimethylsilylbis(indene)etherate (60.3 g, 160.23 mmol) in 189 g THF is added dropwise via a Teflon polymer tubing. The color of the reaction mixture changes immediately to yellow, later red, then red-brown. A yellow solid is forming on the wall of the flask. The temperature rises from 25° C. to 31° C. After ca. 40% of the addition is complete, the temperature is falling back to 25° C. Before the addition is complete, the residue no longer sticks to the wall. After complete addition, the reaction mixture is stirred an additional 16 hours. Then the reaction mixture is brought back into the dry box and filtered through a medium glass frit. The yellow solid is washed twice with 10 mL toluene and once with 10 mL THF. Then it is dried in vacuum. The green filtrates are discarded. Isolated solid 70.3 g (90.8% crude yield). The content of dimethylsilylbis(indenyl)zirconium dichloride was determined to be between 84 and 87 wt %, which corresponds to a yield of dimethylsilylbis(indenyl) zirconium dichloride between 82 and 85%.

EXAMPLE 3

Preparation of dimethylsilylbis(2-methylindenyl) zirconium dichloride via toluene/THF $ZrCl_4$ (31.6 g 0.136 mol) was slurried in 234 g anhydrous toluene. The slurry was stirred for 10 minutes, and then pyridine (21.08 g, 0.266 mol) was added dropwise over 5 minutes. The slurry was stirred for 2.5 hours, and then a THF solution of dilithium salt of dimethylsilylbis(2-methylindene)($Et_2O$) (53.71 g, 0.133 mol; 186 g THF) was added dropwise over 1 hour. An orange solid precipitated. The reaction was stirred overnight. The orange solids were then filtered on a coarse frit, washed with 135 ml toluene, and dried in vacuo. The yield of crude dimethylsilylbis(2-methylindenyl)zirconium dichloride product was 59.46 g (92.8%). The crude product was then suspended in 261 g of THF and heated to 60° C. for 5.5 hours. The slurry was allowed to cool to room temperature, and then filtered on a coarse frit. The orange solid was washed with 100 ml of THF, then dried in vacuo. The purified yield was 34.80 g (54.32%). $^1H$ NMR in $CDCl_3$ revealed a pure product composed of 96.1% racemic and 3.9% meso diastereomers.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended, formed in situ, or mixed with one or more other substances, components and/or ingredients in accordance with the present disclosure. The fact that the substance, component or ingredient may have lost its original identity through a chemical reaction or transformation during the course of such contacting, blending, formation in situ, or mixing operations is thus wholly immaterial for an accurate understanding and appreciation of this disclosure and the claims thereof.

Each and every patent or other publication referred to in any portion of this specification is incorporated in toto into this disclosure by reference for all purposes, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for preparing a chiral metallocene, which process comprises reacting a salt of an asymmetric bis (cyclopentadienyl) moiety-containing ligand with a tertiary heteroaromatic amine adduct of a transition, lanthanide or actinide metal halide in an organic solvent or diluent to produce said chiral metallocene.

2. A process of claim 1 wherein said metal halide is a Group 4–6 metal halide.

3. A process of claim 1 wherein said reaction is performed by adding a solution or slurry of said ligand to a solution or slurry of said adduct.

4. A process of claim 3 wherein said solution or slurry of the ligand is added portionwise to said solution or slurry of the adduct, and wherein the resultant mixture is subjected to agitation.

5. A process of any of claims 1–4 wherein said heteroaromatic amine adduct is formed from pyridine, α-picoline, β-picoline, γ-picoline, quinoline, isoquinoline, quinaldine, acridine, or a mixture of any two or more of these.

6. A process of any of claims 1–4 wherein said ligand comprises a pair of cyclopentadienyl moieties, at least one of which is asymmetric, which are joined by a silicon-containing bridging group.

7. A process of claim 6 wherein said bridging group contains 1–4 atoms and is selected from the group consisting of silanylene, silaalkylene, oxasilanylene and oxasilaalkylene.

8. A process of claim 6 wherein said bridging group is dimethylsilanylene.

9. A process of claim 8 wherein said chiral metallocene is racemic dimethylsilylbis(2-methylindenyl)zirconium dichloride.

10. A process of claim 8 wherein said chiral metallocene is racemic dimethylsilylbisindenyizirconium dichloride.

11. A process of any of claims 1–4 wherein said salt is an alkali metal salt or a magnesium halide salt.

12. A process of any of claims 1–4 wherein said salt is a dilithium salt.

13. A process of claim 12 wherein said heteroaromatic amine adduct is formed from pyridine, α-picoline, β-picoline, γ-picoline, quinoline, isoquinoline, quinaldine, acridine, or a mixture of any two or more of these.

14. A process of claim 1 wherein said ligand is the dilithium salt of a dimethylsilylbis(indene) or the dilithium salt of a dimethylsilylbis(2-methylindene), and wherein said adduct is a tertiary heteroaromatic amine adduct of zirconium tetrachloride or zirconium tetrabromide.

15. A process of claim 14 wherein said adduct is a pyridine adduct of zirconium tetrachloride.

* * * * *